(12) United States Patent
Collier (10) Patent No.: US 8,603,321 B2
(45) Date of Patent: Dec. 10, 2013

(54) SYSTEM AND METHOD FOR SEPARATING PARTICLES FROM LIQUID MEDIA

(75) Inventor: Jeffrey Allen Collier, Queen Creek, AZ (US)

(73) Assignee: Energy Derived, LLC, Queen Creek, AZ (US)

( * ) Notice: Subject to any disclaimer, the term of this patent is extended or adjusted under 35 U.S.C. 154(b) by 280 days.

(21) Appl. No.: 13/025,261

(22) Filed: Feb. 11, 2011

(65) Prior Publication Data

US 2012/0205257 A1 Aug. 16, 2012

(51) Int. Cl.
 *C02F 1/465* (2006.01)
 *C02F 1/463* (2006.01)

(52) U.S. Cl.
 USPC .............................. 205/757; 204/670; 204/671

(58) Field of Classification Search
 USPC ......................................................... 205/757
 See application file for complete search history.

(56) References Cited

U.S. PATENT DOCUMENTS

| | | | | |
|---|---|---|---|---|
| 3,959,131 | A * | 5/1976 | Ramirez et al. | 210/707 |
| 3,964,991 | A * | 6/1976 | Sullins | 204/272 |
| 4,101,409 | A | 7/1978 | Austin | |
| 6,482,327 | B1 * | 11/2002 | Mori et al. | 210/695 |
| 6,524,486 | B2 | 2/2003 | Borodyanski et al. | |
| 6,663,766 | B1 | 12/2003 | Adin et al. | |
| 6,800,206 | B2 | 10/2004 | Robinson | |
| 7,462,287 | B2 * | 12/2008 | Berrak et al. | 204/665 |
| 2003/0121864 | A1 * | 7/2003 | Kin et al. | 210/724 |
| 2007/0017874 | A1 | 1/2007 | Renaud | |
| 2010/0170151 | A1 | 7/2010 | Huber | |

OTHER PUBLICATIONS

Xu, et al. Development of an efficient electroflocculation technology integrated with dispersed-air flotation for harvesting microalgae. Journal of Chemical Technology & Microbiology. vol. 85:11. Jun. 25, 2010. (www.interscience.wiley.com) DOI 10.1002/jctb.2457.
Uduman, et al. Dewatering of microalgal cultures: A major bottleneck to algae-based fuels. Journal of Renewable and Sustainable Energy. vol. 2:1. Jan. 12, 2010. DOI:10.1063/1.3294480.
Gao, et al. Electro-coagulation—flotation process for algae removal. Journal of Hazardous Materials. vol. 177, Issues 1-3, May 15, 2010, pp. 336-343. Available online Dec. 29, 2009.
Robinson. Electroflocculation in the Treatment of Polluted Water. 1995. Electropure Australia, Ltd. Wadonga, Victoria Australia. http://www.rotaloo.com/electrofloc.pdf.
Algae Industry Magazine. World Water Works AHTO System for Algae Harvesting. AlgaeIndustryMagazine.com. Feb. 4, 2011. http://www.algaeindustrymagazine.com/world-water-works-ahto-system-for-algae-harvesting/?utm_source=feedburner&utm_medium=email&utm_campaign=Feed%3A+AlgaeIndustryMagazine+%28Algae+Industry+Magazine%29.

* cited by examiner

*Primary Examiner* — Keith Hendricks
*Assistant Examiner* — Salil Jain
(74) *Attorney, Agent, or Firm* — Lisa Foundation Patent Law Clinic (57) ABSTRACT

A system for separating small particles from liquid media comprising: a reactor vessel(s), a hollow primary electrode(s) within the reactor vessel(s), a secondary electrode(s) within the primary electrode(s), an air delivery apparatus configured to deliver coarse air bubbles within the primary electrode(s), an electrical charge apparatus, a separation vessel fluidly coupled to the reactor vessel(s), tertiary electrodes within the separation vessel, and a skimming device configured to collect flocculated material. A method for separating particles from liquid media, comprising the acts of: circulating liquid media throughout a reactor vessel(s), adding coarse air bubbles that travel through a hollow primary electrode(s) to facilitate circulation of the liquid media and removal of micro-bubbles, applying an electrical potential between primary electrode(s) and secondary electrode(s), routing the liquid media to a separation vessel, applying an electrical potential to tertiary electrodes, and skimming flocculated material from an upper surface of the liquid media.

10 Claims, 5 Drawing Sheets

SYSTEM AND METHOD FOR SEPARATING PARTICLES FROM LIQUID MEDIA

BACKGROUND OF THE INVENTION

1. Field of the Invention

The present invention relates to a method for separating particles from liquid media. Specifically, the invention relates to separating microalgae or other small particles from liquid media using electro-flocculation, flotation, and physical separation of flocculated particles from the liquid media.

2. Description of Related Art

A major bottleneck for processing microalgae for use in bio-fuels, food supplements, and other products is separating the microalgae from the liquid growth medium. Two of the major methods currently used involve filtration or centrifugation. In the case of filtration, filters are frequently clogged by the microalgae. As a result, filter maintenance becomes costly and labor-intensive. Centrifugation, on the other hand, is very energy-intensive. Separating microalgae from liquid growth medium without the high costs of maintenance, labor, or energy would be highly beneficial. It would greatly raise the level of efficiency for harvesting microalgae. Thus, microalgae would become a more viable source of fuel as an alternative to fossil fuels. Additionally, such an invention may be useful in other applications, such as waste-water treatment. There are some prior art references that attempt to address these efficiency problems using a electro-flocculation and/or flotation, but they fall short of providing a system that provides an affordable, long term, commercially viable method of separating high concentrations of particles from a liquid media.

So as to reduce the complexity and length of the Detailed Specification, and to fully establish the state of the art in certain areas of technology, Applicant herein expressly incorporates by reference all of the following materials identified in each numbered paragraph below.

U.S. Pat. No. 6,663,766 to Adin et al. describes a water purification process for making potable water wherein impure water enters the bottom of a vessel and purified water exits the top of the vessel. U.S. Pat. No. 6,800,206 to Robinson describes using electro-flocculation for treating water in a reaction vessel where the pollutants are removed from the top of the reaction vessel. These inventions would be inadequate for large scale removal of flocculated particles because they are only intended to remove very low concentrations of pollutants from water and are not suitable for removing high concentrations of particles.

U.S. patent application Ser. No. 11/184,733 by Renaud describes a method for separating contaminants from an aqueous medium wherein the effluent, after being mixed with a flocculent, is allowed to settle in a vessel. The sludge that rises to the top is then removed by a device using a vacuum. This application teaches using a vacuum system for harvesting. Such construction, while perhaps useful in some situations, is not necessary for efficient harvesting and therefore unnecessarily increases the complexity of the device. Furthermore, this application erroneously overlooks the complexity and potential for improvement in the processes of electrocoagulation and electroflocculation. In reality, the complex vacuum separation column taught by this application would not be necessary if the electrocoagulation and electroflocculation step were carried out in a more efficient manner.

U.S. Pat. No. 4,101,409 to Austin describes an apparatus for treating sludge involving adding the sludge to a vessel, applying a current to metal plates in a vessel, and supplying pressurized air to the vessel in order to help the sludge float to the top. Austin also describes using a mechanized paddle system on a conveyor belt to remove the sludge that has floated to the top of the vessel. This invention incorporates the flocculation and separation into one vessel, which increases the complexity and reduces efficiency since the two actions are mutually inhibitive, i.e., flocculation is improved by increasing agitation while separation is improved by minimizing agitation.

U.S. Pat. No. 6,524,486 to Borodyanski et al. describes using a telescopic froth-flotation column for separating microalgae from a liquid suspension. A flocculating agent is added to the suspension and the suspension is added to the column as air bubbles are forced up the column. This invention describes using a chemical flocculating agent (like starch, ferric chloride, aluminum sulphate, or ketosones at a rate of 100-300 grams per ton of algae). This invention is not conducive to using electro-flocculation. Therefore, for the water to be recycled through the system, it must be subjected to a costly treatment. Alternatively, fresh water could be introduced for each batch of microalgae, but that is an economically inefficient use of water.

Applicant believes that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), applicant will amend the specification to expressly recite the essential material that is incorporated by reference as allowed by the applicable rules.

BRIEF SUMMARY OF THE INVENTION

The present invention provides among other things a system and method for separating small particles from liquid media by utilizing electro-flocculation in a reaction vessel, flotation in a separation vessel, and using a skimming device to harvest flocculated material.

It is an object of the invention to provide a system and method for separating small particles from liquid media.

The above and other objects may be achieved using systems involving at least one reactor vessel, at least one hollow primary electrode within the reactor vessel(s), one secondary electrode within the hollow primary electrode(s), and at least one air delivery apparatus with at least one terminal substantially at a base of the hollow primary electrode(s), wherein the air delivery apparatus(i) is/are configured to deliver coarse air bubbles to an inner space within the hollow primary electrode(s) when the reactor vessel(s) is/are substantially filled with liquid media. Furthermore, such systems involve an electrical charge apparatus electronically coupled to the hollow primary electrode(s) and the secondary electrode(s), so that an electronic potential is generated between a hollow primary and a secondary electrode. Additionally, such systems involve a separation vessel fluidly coupled to the reactor vessel(s), at least one tertiary electrode coupled to the separation vessel, and a skimming device configured to collect a flocculated material when the flocculated material floats to an upper surface of liquid media in the separation vessel.

The above and other objects may be achieved using methods involving circulating liquid media throughout at least one reactor vessel and adding coarse air bubbles to the liquid media in the reactor vessel(s) such that at least some of the coarse air bubbles travel upward through at least one hollow primary electrode within the reactor vessel(s), facilitating the removal of micro-bubbles from the liquid media. Furthermore, such methods involve applying an electrical potential between the hollow primary electrode and a secondary electrode within the hollow primary electrode, such that ions are dispersed throughout the liquid media, causing a net electrostatic charge of at least one particle within the liquid media to change. Such methods also involve routing the liquid media from the reactor vessel(s) to a separation vessel, applying an electrical potential to at least one tertiary electrode coupled to the separation vessel wherein the electrical potential generates micro-bubbles that attach to flocculated material in the liquid media and cause the flocculated material to float to an upper surface of the liquid media, and skimming the flocculated material that has floated to the upper surface of the liquid media with a skimming device.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. §112, ¶6. Thus, the use of the words "function," "means" or "step" in the Detailed Description or Description of the Drawings or claims is not intended to somehow indicate a desire to invoke the special provisions of 35 U.S.C. §112, ¶6, to define the invention. To the contrary, if the provisions of 35 U.S.C. §112, ¶6 are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. §112, ¶6. Moreover, even if the provisions of 35 U.S.C. §112, ¶6 are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Figures 1, 2:
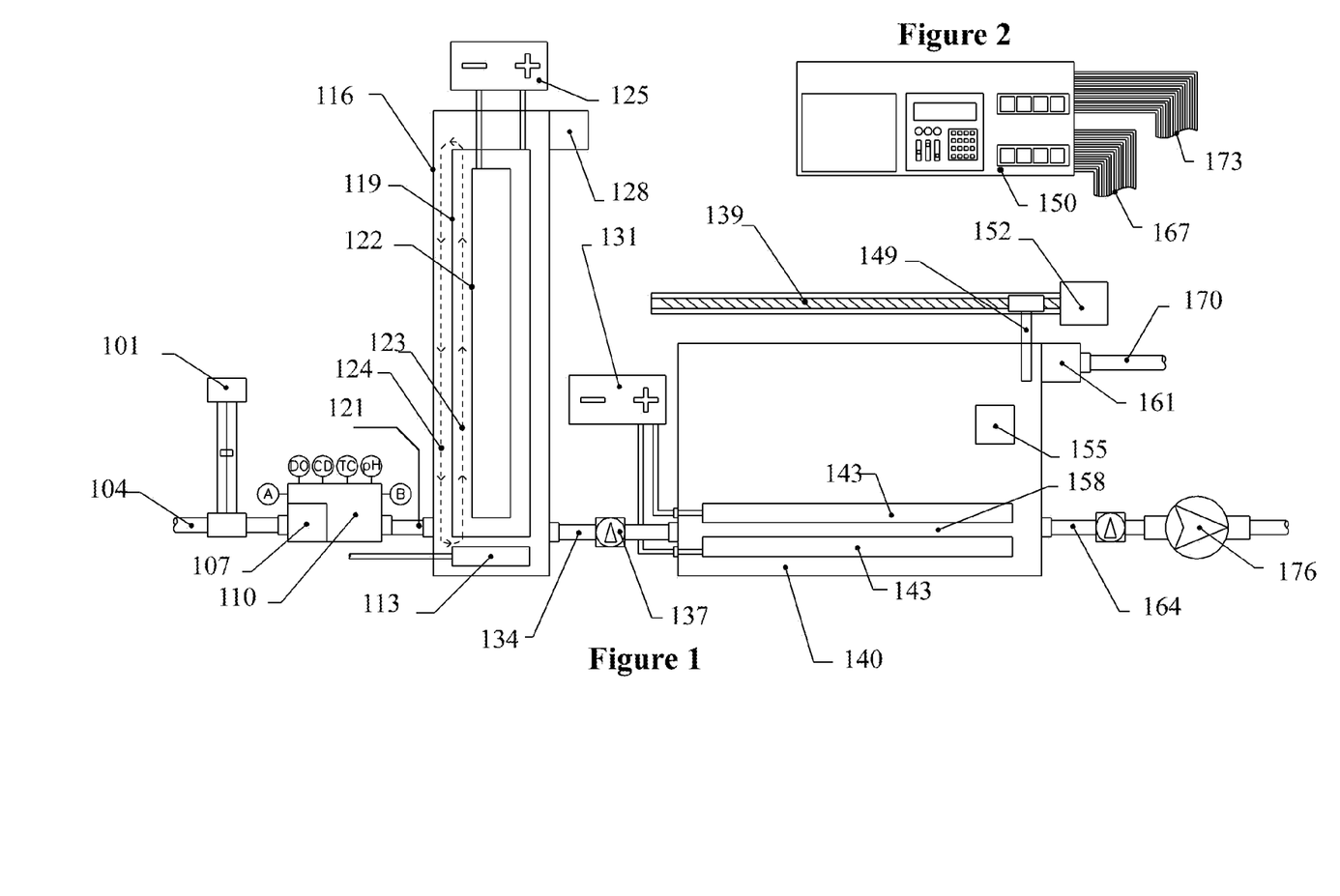
FIG. 1 depicts a side view of an embodiment of the system.
FIG. 2 depicts a side view of a control console that can be incorporated into the system.

A preferred embodiment of the invention is shown in FIG. 1, which is described in the context of harvesting algae from batches of influent liquid media. In this embodiment, the influent liquid media is an algae growth media. In a suitable algae harvesting application, the algae growth media may be contained in a photobioreactor—such as a closed system, an open pond, or some other photobioreactor—before being introduced into to the system through an inlet 104. Depending on the type of photobioreactor used, gravity, a pump, or other means may be used in conjunction with the inlet 104 to transfer the algae growth media into the reactor vessel 116. A person of ordinary skill in the art would have sufficient knowledge to devise such a transfer system, or the transfer system may be prefabricated and integrated with the system.

In some implementations, a control console 150, as shown in FIG. 2, may be used in conjunction with the system. Such a control console 150 may be electrically coupled to sensor inputs 167 and process control outputs 173. Sensor inputs may be coupled to sensing devices such as, but not limited to, a flow sensor 101, fluid level sensors 128 and 161, influent processing sensors 110, or other processing sensors 155. Processing sensors 110 and 155 may monitor parameters such as, but not limited to, optical density, pH, or electrical conductivity of liquid media. Furthermore, an optical processing monitor 107 may be used to provide feedback independently or in conjunction with a control console 150.

Reactor Vessel

Figure 3:
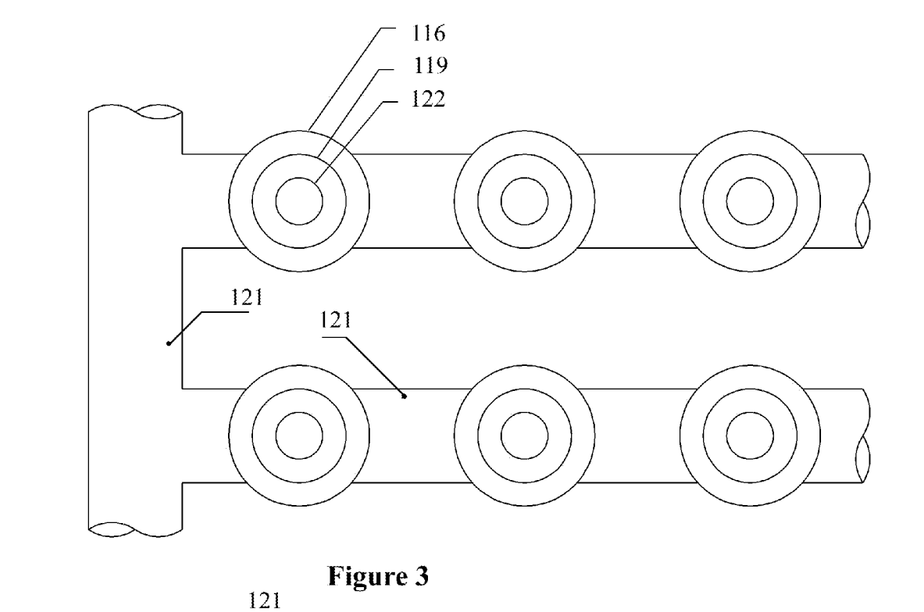
FIG. 3 depicts a top view of several reactor vessels connected in series-parallel, with other related elements.
Figure 4:
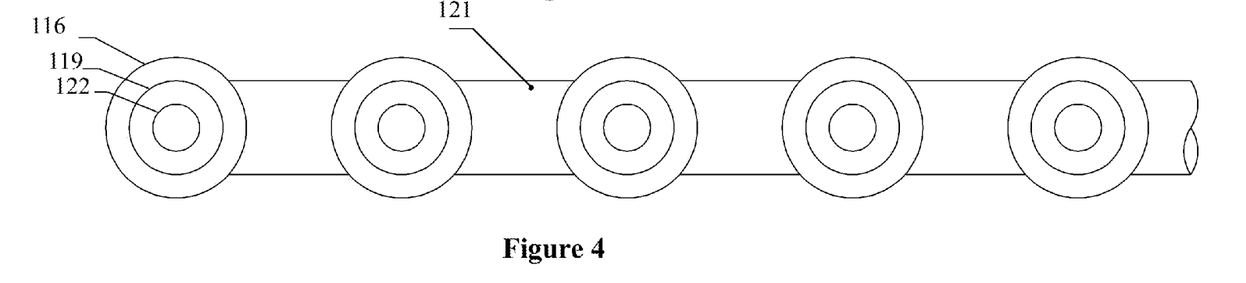
FIG. 4 depicts a top view of several reactor vessels connected in series, with other related elements
Figure 5:
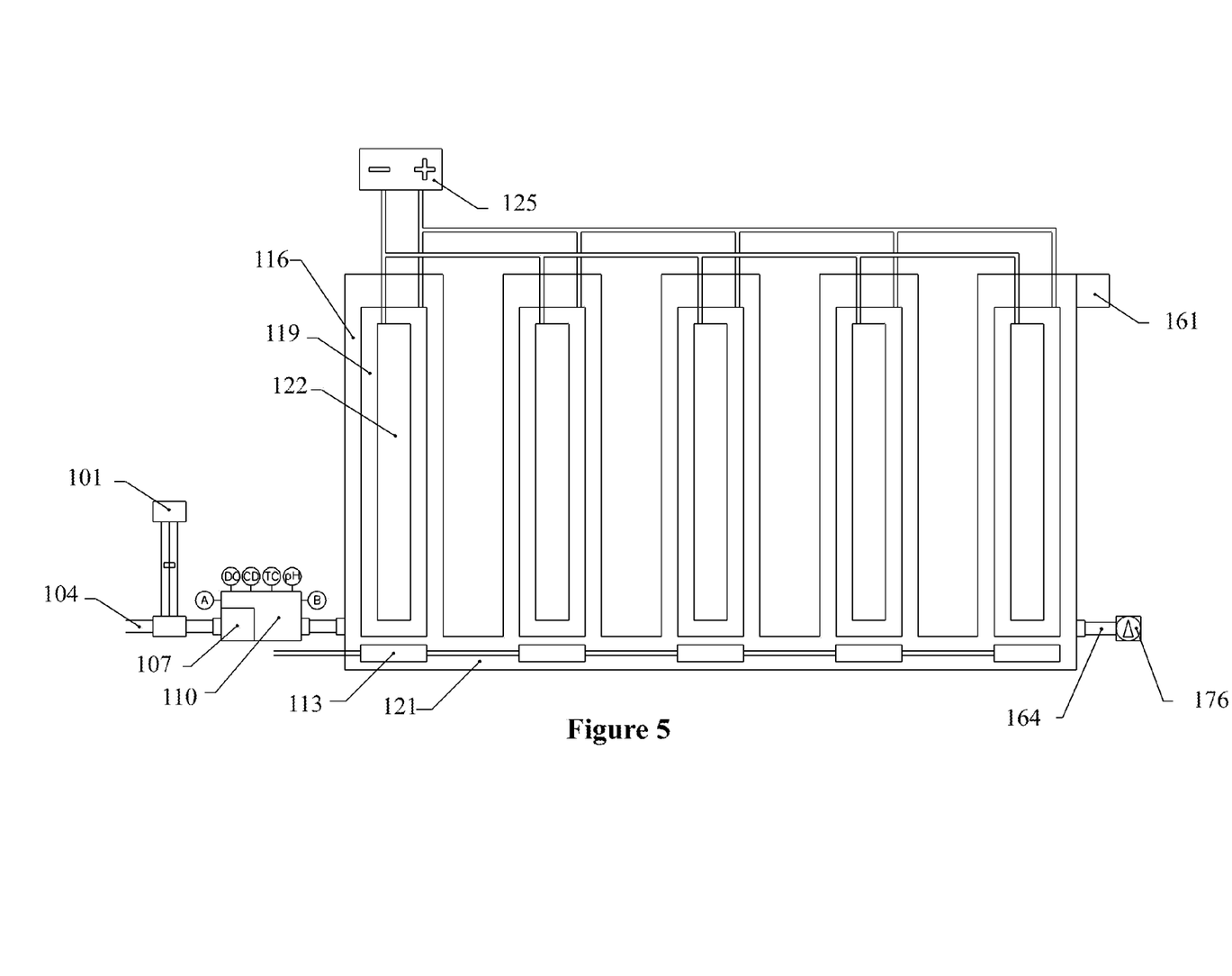
FIG. 5 depicts a side view of several reactor vessels connected in series, with other related elements.

In some implementations of the invention, as shown in FIGS. 3 and 4, several reactor vessels 116 are used in order to increase both the volumetric capacity per batch and the surface area of electrodes 119 and 122 exposed to the algae growth media. The several reactor vessels 116 may be coupled in series via a common pipe or other appropriate conduit 121. The common pipe or other appropriate conduit 121 may be oriented substantially parallel to the ground. The reactor vessels 116 may be coupled to the common pipe or other appropriate conduit 121 at the base of the reactor vessels 116, but a person of ordinary skill in the art may elect to attach the common pipe or other appropriate conduit 121 at any point on the reactor vessels 116, 901.

In some implementations of the invention, the reactor vessels 116 are coupled in series, as shown in FIGS. 4 through 8, in order to provide an efficient overall shape of the whole system or to increase throughput or for some other reason. Alternatively, a person of ordinary skill in the art may elect to couple the reactor vessels 116 in parallel or with several groups of vessels coupled in series wherein each group is coupled to each other group in parallel (series-parallel), as shown in FIG. 3. Furthermore, a person of ordinary skill in the art may elect to use only one reactor vessel 116, as shown in FIG. 1.

Figure 6:
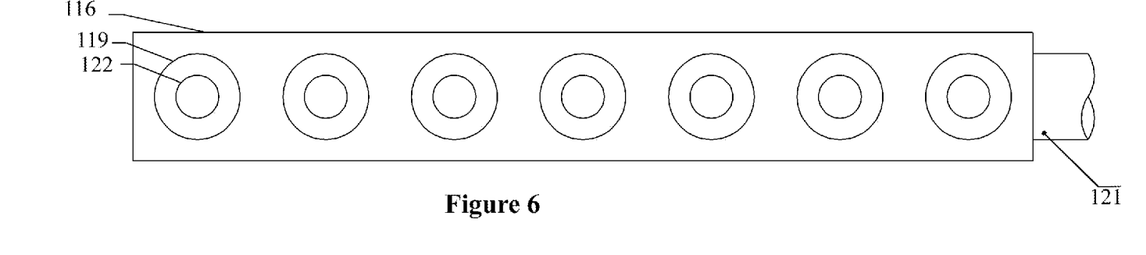
FIGS. 6-8 depict some configurations of reactor vessels.
Figure 7:
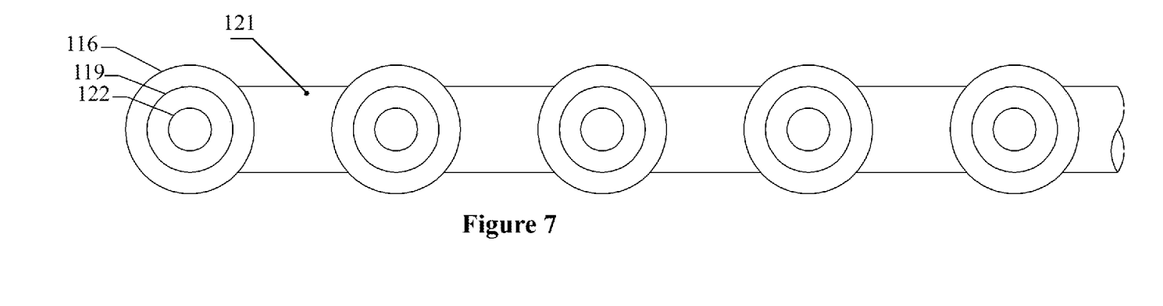
Figure 8:
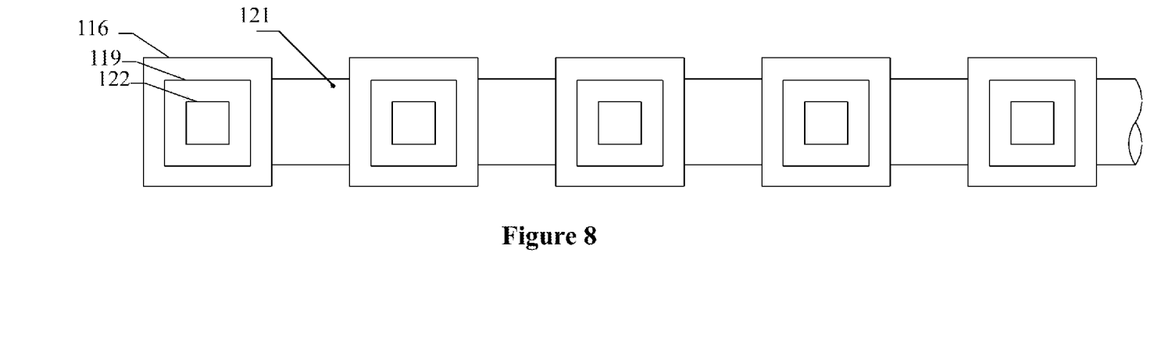

In some implementations, each reactor vessel 116 may be cylindrical as shown in FIG. 7. A person of ordinary skill in the art would know that any other suitably shaped reactor vessel 116 may be used, such as the non-limiting examples shown in FIGS. 6 and 8. Each reactor vessel may be coupled to the common pipe or other appropriate conduit 121 at substantially a right angle and extend vertically upward, away from the common pipe or other appropriate conduit 121.

In some implementations, the overall shape and size of the system are such that the system may be carried on or made part of a mobile vehicle. For example, the system may have a shape and size that would be adequate for carrying the system on a towable trailer. This is done so that one whole system may be used in conjunction with a mobile vehicle In some implementations, the system is permanently or semi-permanently constructed in a fixed location. In such a case, size and shape requirements are not as restrictive as with a when suing the system with a mobile vehicle.

Hollow Primary Electrode and Secondary Electrode

In some implementations, as shown in FIGS. 1, 3, 4, 5, 7, and 8, one set of electrodes comprising one hollow primary electrode 119 and one secondary electrode 122 is contained at least partially within each reactor vessel 116. Each hollow primary electrode 119 may be, for example, a cylindrical aluminum tube. Each secondary electrode 122 may be, for example, a solid, cylindrical aluminum rod. However, a person of ordinary skill in the art would know that other geometries could be used. Furthermore, a person of ordinary skill in the art would know that the secondary electrode 122 may be at least partially hollow.

In some implementations, at least one reactor vessel 116 and its corresponding hollow primary electrode 119 and secondary electrode 122 may be oriented, as shown in FIG. 7, for example, as follows: the secondary electrode 122 is contained at least partially within the hollow primary electrode 119, which is contained at least partially within the reactor vessel 116. The reactor vessel 116, hollow primary electrode 119, and secondary electrode 122 may be aligned coaxially, with the secondary electrode 122 comprising the axis.

At an end proximal to the common pipe or other appropriate conduit 121, both electrodes 119 and 122 may extend further than the reactor vessel 116 into the common pipe or other appropriate conduit 121, such that when the pipe 121 and vessel 116 are filled with liquid media, the surface area of electrodes 119 and 122 exposed to the liquid media is maximized. At an end distal from the common pipe or other appropriate conduit 121, both electrodes 119 and 122 may extend substantially to the end of the reactor vessel 116 that is distal from the common pipe or other appropriate conduit 121.

In some implementations, the hollow primary electrode 119 and secondary electrode may be comprised of aluminum 122. This material may be suitable due to its relatively low price and high availability, together with its ability to form positively charged ions when submersed in an aqueous solution and subjected to an electrical potential. A person of reasonable skill in the art would know that other materials could be used. For example, aluminum alloys, magnesium, magnesium alloys, or any other metal or other material that can form positively charged ions when submersed in an aqueous solution and subjected to an electrical potential could be used.

In some implementations, any hollow primary electrodes 119 and secondary electrodes 122 may be coupled to a reactor vessel 116 and/or to each other. For example, a non-conductive separation collar may be used to secure the electrodes 119 and 122 in place within the reactor vessel 116, such that each electrode 119 and 122 is electrically isolated.

In some implementations, the hollow primary electrodes 119 and secondary electrodes 122 may be electrically coupled to an electrical charge apparatus 125, as shown in FIG. 1, that can provide an electric potential and current which may be controlled by a user. For example, such an electrical charge apparatus 125 may be coupled to a control console 150. A person of ordinary skill in the art would be able to optimize the potential and current depending on, among other things, conductivity of the liquid media, particle density, size of electrodes 119 and 122, or type of material used in the electrodes 119 and 122. One example of a basis for optimization is maximizing the rate at which ions are distributed from the electrodes 119 and 122 to the liquid media and circulated, while minimizing the number of ions that are distributed into the liquid media but not used to neutralize a charge of a suspended particle such as a cell of microalgae. Influent processing sensors 110 may be incorporated into the system in order to provide feedback to the user, which may be used for further optimization. Furthermore, a person of ordinary skill in the art would know that the diameter and thickness of the primary hollow 119 and secondary 122 electrodes could also be varied.

In some implementations, as shown in FIG. 6, a plurality of sets of electrodes comprising one hollow primary electrode 119 and one secondary electrode 122 may be contained within a reactor vessel 116. In some implementations, a plurality of hollow primary electrodes 116 may be used with each secondary electrode 122, or a plurality of secondary electrodes 122 may be used with each hollow primary electrode 116. The surfaces of the electrodes 119 and 122 may be oriented, for example, such that the surfaces of the electrodes 119 and 122 are parallel, separated equidistant, and/or concentric. For example, two hollow primary electrodes 119 may be used with one secondary electrode 122. In this case, the secondary electrode 122 is contained within a second of the two hollow primary electrodes 119, which is contained within a first of the two hollow primary electrodes 199.

Figure 9:
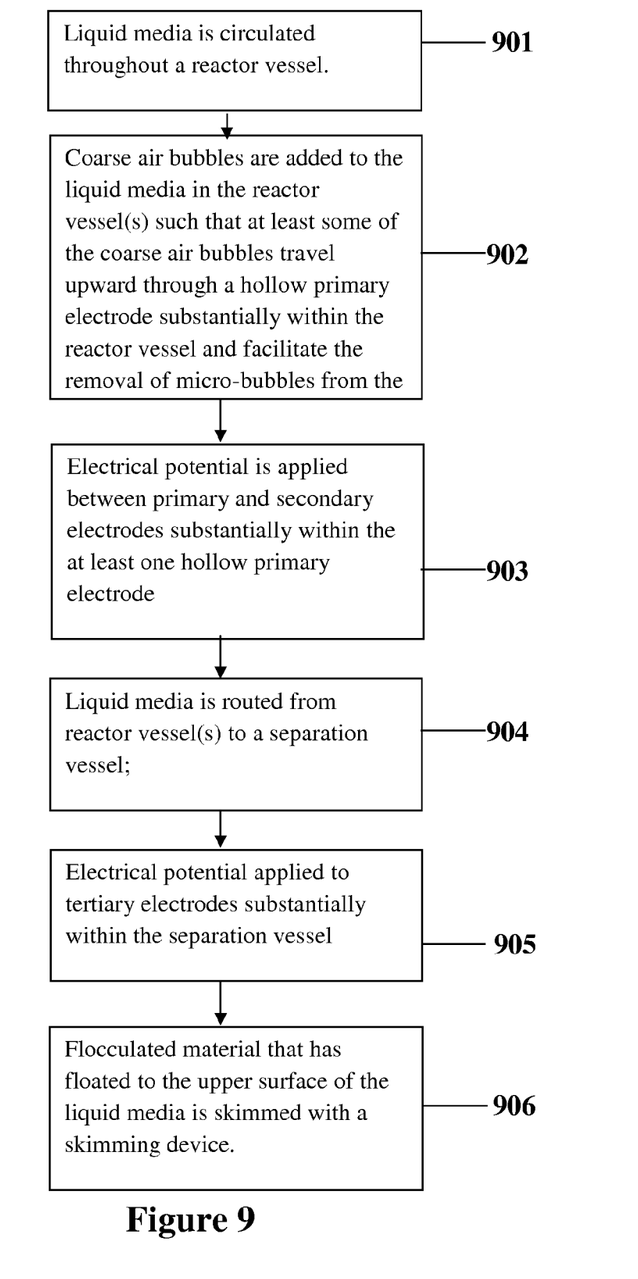
FIG. 9 depicts a method for separating small particles from liquid media.

In some implementations, a person of ordinary skill in the art may elect to alternate the polarity of adjacent electrodes. This may be done in order to generate an electric field between adjacent electrodes. For example, if one hollow primary electrode 119 is used in conjunction with one secondary electrode 122, the hollow primary electrode may be given a positive charge while the secondary electrode is given a negative charge by the electrical charge apparatus 125, or vice-versa. Additionally, the polarity of each electrode 119 and 122 may be fixed, alternated once, or alternated more than once over time 903.

Air Delivery Apparatus

Coarse air bubbles may be used to facilitate removal of micro-bubbles from the liquid media in the reactor vessel and aid in circulating the liquid media in the reactor vessel. The following are some non-limiting examples of how a person of ordinary skill in the art may elect to configure an air delivery apparatus 113 to substantially accomplish such purposes.

In some implementations, an air delivery apparatus 113 is coupled to at least one reactor vessel 116. The air delivery apparatus 113 may be configured to deliver coarse air bubbles into the liquid media. This delivery may be configured to occur either automatically or through manual control. The source of air for the air delivery apparatus 113 may be, but is not limited to, bottled compressed air, or an air compressor. The air delivery apparatus 113 may be further coupled to a regulator configured to monitor and control the pressure of the air in the air delivery apparatus. The air delivery apparatus may be coupled to the reactor vessel 116 at the base of the reactor vessel or at some other location that a person of ordinary skill in the art may elect. For example, depending on the implementation, the air delivery apparatus may be coupled to the base of the reactor vessel or the common pipe or other appropriate conduit 121 directly below the hollow primary electrode 119 such that, when coarse air bubbles are delivered into the liquid media, the coarse air bubbles travel upward through the hollow primary electrode 119. In such an example, as shown in FIG. 1, the motion of the coarse air bubbles would may cause liquid media 123 inside the hollow primary electrode 119 to flow upward, while the liquid media outside 124 the hollow primary electrode 119 would flow downward.

In some embodiments, a person of ordinary skill in the art may choose to use an air delivery conduit, comprised of a plastic tube, for example, to transfer air from the air delivery apparatus into the reactor vessel 116. Such an air delivery conduit may be oriented in any manner that a person of ordinary skill in the art may devise in order to deliver the coarse air bubbles into the reactor vessel 116. For example, such an air delivery conduit may be inserted through the end of the reactor vessel 116 distal from or proximate to the common pipe or other appropriate conduit 121, or anywhere in between. Such an air delivery conduit may extend from the air delivery apparatus 113 and terminate within and near the end of the hollow primary electrode proximal to the common pipe or other appropriate conduit 121, 902.

Separation Vessel

The liquid media may be transferred to a separation vessel 140, as shown in FIG. 1, to facilitate the separation and subsequent removal of small particles in the liquid media. In some implementations, the separation vessel may be coupled to a common pipe or other suitable conduit 121. In other cases, for example, a conduit 134 other than the common pipe or other suitable conduit 121 may be used. In order to facilitate transfer of the liquid media from the at least one reactor vessel 116 to the separation vessel 140, gravity, a pump, or any other device for transferring fluid may be used. In some implementations, a valve 137 is utilized between the at least one reactor vessel 116 and the separation vessel 140. Such a valve may be manual or automatically controllable, and may be coupled to a control console 150.

In some implementations, the separation vessel 140 is comprised of a substantially transparent material such as polycarbonate or poly(methyl methacrylate). In some implementations, translucent or opaque material may be used, such as polyvinyl chloride, polyethylene, polypropylene, or acrylonitrile butadiene. In some implementations other types of plastics are used. These are non-limiting examples, and a person of ordinary skill in the art would know that many other materials exist or may be discovered which can contain liquid and would, therefore, be suitable for the separation vessel 140. Furthermore, any material that could be used in the composition of the separation vessel 140 could also be used in the composition of the at least one reactor vessel 116.

A person of ordinary skill in the art would know that a partitioned separation vessel, a partition-able separation vessel, or two or more separation vessels may be used to accomplish the purpose of facilitating the separation and subsequent removal of small particles in the liquid media 904.

Tertiary Electrode

In some implementations, at least one tertiary electrode 143 may be substantially within the separation vessel 140. The at least one tertiary electrode 143 may be coupled to the side or some other suitable location on or about the separation vessel 140. The at least one tertiary electrode 143 may be electrically coupled to an electrical charge apparatus 131, as shown in FIG. 1, that can provide an electric potential and current which may be controlled by a user. For example, such an electrical charge apparatus 131 may be coupled to a control console 150. A person of ordinary skill in the art would be able to optimize the potential and current depending on, among other things, conductivity of the liquid media, particle density, size of tertiary electrodes 143, or type of material used in the tertiary electrodes 143. In some implementations, tertiary electrodes 143 may be used in pairs such that one of each pair is given a positive charge and the other is given a negative charge. Such a configuration may be selected to substantially balance the number of anodes and cathodes, but a person of ordinary skill in the art would know that such balancing is not crucial to the operation of the tertiary electrodes 143. Furthermore, in some implementations, geometries of the tertiary electrodes 143 may be selected to maximize surface area, but a person of ordinary skill in the art would know that such maximization is not crucial, and other considerations may be taken into account. Such considerations may be, but are not limited to, cost, availability, and physical limitations of the tertiary electrodes 143.

In some implementations, the at least one tertiary electrode 143 may be comprised of carbon. As a first objective, a preferred material would be one that does not form ions when submersed in an aqueous solution and subjected to an electrical potential. As a second objective, a preferred material would be one that causes micro-bubbles 158, such as hydrogen, for example, to form when the electrode 143 is submersed in an aqueous solution and subjected to an electrical potential. A person of ordinary skill in the art would know that there are several other materials in existence or that may be developed besides or in addition to carbon that may be used to accomplish the first and second objectives. Furthermore, the first and second objectives may have varying degrees of importance, and there may also be other objectives that may be weighed with these first and second objectives. For example, to the extent that adding ions to the liquid media in the separation vessel is not a principal concern, a person of ordinary skill in the art may choose to use a material that forms ions when submersed in an aqueous solution and subjected to an electrical potential. Such a material may be one similar to that which comprises the hollow primary 119 or secondary 122 electrodes 905.

Skimming Device

In some implementations, a skimming device, comprising 139, 149, and 152 as shown in FIG. 1, is configured to operate in conjunction with the separation vessel 140. A non-limiting example of such a device may comprise a paddle 149 with the following dimensions: a width substantially equal to an interior width of the separation vessel 140 and a height sufficient to pass through an accumulation of flocculated material when a substantial portion of the flocculated material has floated to and accumulated at the upper surface of the liquid media. In this example, the paddle 149 may be coupled to a moveable arm. The moveable arm, or the paddle 149, may be coupled to an actuator 139, which may be coupled to a motor 152 or other means of supplying energy. Examples of actuators 139 include, but are not limited to, a ball screw, a roller screw, a belt drive, a chain drive, a rack and pinion, a winch, a hoist, a pneumatic actuator, or a hydraulic actuator. Additionally, more than one paddle 149 may be used 906.

Separation Vessel Effluent

In some implementations, a collection vessel may be coupled, for example, by a concentrated floc conduit 170 as shown in FIG. 1, to the separation vessel and may be used in conjunction with the skimming device 139, 149, and 152 to facilitate collection of flocculated material. Furthermore, a liquid media outlet pipe or other suitable conduit 164 may be used for draining liquid media from the separation vessel 140 after a substantial portion of the flocculated material has been skimmed. For example, a liquid media outlet pipe 164 may be coupled to the separation vessel 140 that would facilitate recycling liquid media back into a photobioreactor. Fluid flow from the separation vessel may be facilitated, for example, by a pump 176.

In some implementations, the system may be designed to permit further processing of the liquid media in an additional reactor vessel or set of reactor vessels. The system may be designed to permit further processing of the concentrated flocculated material in an additional separation vessel or set of separation vessels, for example.

I claim:

1. A system for separating small particles from liquid media, comprising:
    at least one reactor vessel;
        at least one hollow primary electrode substantially within the at least one reactor vessel;
        at least one secondary electrode substantially within the at least one hollow primary electrode;
        at least one air delivery apparatus configured to deliver coarse air bubbles to an inner space within the at least one hollow primary electrode when the at least one reactor vessel is substantially filled with liquid media;
        an electrical charge apparatus electronically coupled to the at least one hollow primary electrode and the at least one secondary electrode;
    a separation vessel fluidly coupled to the at least one reactor vessel;
    at least one tertiary electrode substantially within the separation vessel; and
    a skimming device configured to collect a flocculated material when the flocculated material floats to an upper surface of liquid media in the separation vessel.

2. The system of claim 1, wherein the at least one air delivery apparatus is configured to deliver the coarse air bubbles at a rate sufficient to cause particles in particle-containing liquid media to flow upward through the at least one hollow primary electrode when the at least one reactor vessel is substantially filled with particle-containing liquid media.

3. The system of claim 1, wherein at least one of the at least one hollow primary electrode and the at least one secondary electrode is comprised of a metal.

4. The system of claim 1, wherein at least one of the at least one hollow primary electrode and the at least one secondary electrode is comprised of a metalloid.

5. The system of claim 1, wherein the at least one tertiary electrode is comprised of carbon.

6. The system of claim 1, wherein the at least one tertiary electrode is coupled to an end of the separation vessel and is substantially contained within the separation vessel.

7. The system of claim 1, further comprising at least a second reactor vessel, wherein the at least two reactor vessels are fluidly coupled in series.

8. The system of claim 1, wherein the at least two reactor vessels are fluidly coupled in parallel.

9. The system of claim 1, wherein the at least two reactor vessels are fluidly coupled in series-parallel.

10. The system of claim 1, wherein the flocculated material is comprised of microalgae.

* * * * *